United States Patent [19]

Fletcher et al.

[11] 4,003,257
[45] Jan. 18, 1977

[54] ANALYSIS OF VOLATILE ORGANIC COMPOUNDS
[76] Inventors: James C. Fletcher, Administrator of the National Aeronautics and Space Administration, with respect to an invention of Albert Zlatkis, Houston, Tex.
[22] Filed: Mar. 12, 1974
[21] Appl. No.: 450,504
[52] U.S. Cl. .............................. 73/23.1; 23/230 R; 23/230 B; 23/230 M; 23/231; 23/232 R; 23/232 C; 23/254 R; 55/67; 55/74; 55/197; 73/61.1 C
[51] Int. Cl.² ................ G01N 31/06; G01N 31/08; G01N 33/02; G01N 33/16
[58] Field of Search ........ 23/230 R, 230 B, 230 M, 23/232 R, 232 C, 254 R, 231; 73/23.1, 61.1 C; 55/197, 67, 74

[56] References Cited
UNITED STATES PATENTS

| 3,352,089 | 11/1967 | Modell et al. | 55/197 X |
|---|---|---|---|
| 3,357,158 | 12/1967 | Hollis | 55/197 X |
| 3,581,465 | 6/1971 | Haruki et al. | 55/67 |
| 3,715,910 | 2/1973 | Fore et al. | 23/230 M X |
| 3,807,217 | 4/1974 | Wilkins et al. | 73/23.1 |
| 3,836,332 | 9/1974 | James | 23/230 B |
| 3,847,546 | 11/1974 | Paul | 23/230 PC |
| 3,924,219 | 12/1975 | Braun | 23/254 E |

OTHER PUBLICATIONS

Hovermann and Jecht, "Ein Gas–chromatographisches Geratesystem fur Automatische Spurenbestimmungen," Technical Publication of Siemens AG., Oct. 1973.
Treybal, "Mass Transfer Operations," 2nd Edition, pp. 548–550 (1968).
Van Wilk, J. Chromatographic Science, vol. 8, pp. 418–420, July 1970.
Teranishi et al., Anal. Chem., vol. 44, No. 1, pp. 18–20, Jan. 1972.
Zlatkis, et al., Chromatographia, vol. 6, No. 2, pp. 67–70, Feb. 1973.
Zlatkis, et al., Anal. Chem. vol. 45, No. 4, pp. 763–767, Apr. 1973.
Zlatkis, et al., J. Chromatographic Science, vol. 11, pp. 299–302, June 1973.
Zlatkis, et al., Clinical Chemistry, vol. 17, No. 7, pp. 592–594, 1971.

*Primary Examiner*—Norman Yudkoff
*Assistant Examiner*—Barry I. Hollander
*Attorney, Agent, or Firm*—Russell E. Schlorff; John R. Manning; Marvin F. Matthews

[57] ABSTRACT

System and method for reproducibly analyzing, both qualitatively and quantitatively, trace amounts of a large number of organic volatiles existing in a gas sample. Applications include (1) analyzing the headspace gas of body fluids and comparing a profile of the oganic volatiles with standard profiles for the detection and monitoring of disease, (2) analyzing the headspace gas of foods and beverages and comparing a profile of the organic volatiles with standard profiles so that flavor and aroma can be monitored and controlled, and (3) similar analysis for determining the organic pollutants in samples of water and air.

The system includes a novel means (sample trap) for capturing and enriching the organic volatiles, a novel injector port for directly injecting the entrapped organic volatiles to a cryogenic percolumn to provide a sharply defined plug, and a novel capillary separating column. Various detectors may be utilized to identify the separated volatiles.

The sample trap contains a solid adsorbent having the following properties: (1) high affinity for volatile organic compounds, (2) hydrophobic, (3) temperature stability up to 400° C, (4) good desorption capability and (5) relative inertness to the sample. A porous material based on a polymer of 2,6-diphenyl-p-phenylene oxide (PPPO) and sold under the trademark TENAX-GC is particularly suited for this purpose. The injector port is formed of a hollow body having inlet and outlet ports. The sample trap is inserted into the body and maintained in sealed engagement with the outlet port. The injector port is placed into an injector heater of a gas chromatograph (GC) to effect desorption of the entrapped volatiles. Helium gas is introduced at the inlet port to carry the organic volatiles directly into the cryogenic precolumn. The GC capillary separating column is formed of etched nickel which facilitates the separation of a large number of specific organic compounds from a very small amount of organic volatiles.

36 Claims, 11 Drawing Figures

COMPARISON OF URINARY VOLATILE ORGANIC COMPOUNDS FROM NORMAL AND DIABETIC INDIVIDUALS

SULFUR VOLATILES

COMPARISON OF URINARY VOLATILE ORGANIC SULFUR COMPOUNDS FROM NORMAL AND DIABETIC INDIVIDUALS

VOLATILE ORGANIC COMPOUNDS IN NORMAL HUMAN BREATH

VOLATILE ORGANIC COMPOUNDS IN HOUSTON, TEXAS, AIR

Fig. 9 SULFUR VOLATILES FROM CIRRHOSIS URINE

Fig. 10 SULFUR VOLATILES FROM COFFEE

Fig. 11

SULFUR VOLATILES FROM CIGARETTE SMOKE

ANALYSIS OF VOLATILE ORGANIC COMPOUNDS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; U.S.C. 2457).

BACKGROUND OF THE INVENTION

1. Field of the Invention

The present invention relates to improved analytical techniques and means for reproducibly analyzing trace quantities of a wide range of volatile organic compounds and the application of such techniques to the detection of metabolic disorders, flavor and aroma analyses, air and water pollution analyses, petroleum exploration, etc.

2. Description of the Prior Art

The introduction of gas chromatography and detector technology has provided analytical techniques especially suitable for trace analysis of organic substances. A mass spectrometer can be considered to be a specific detector for a gas chromatograph, and its performance can be adjusted according to the needs of the analysis, thus providing an excellent fingerprint or profile of a chemical substance. This technique lends itself to computerization with all its inherent advantages. For example, files containing some 300,000 organic compounds are available even for small laboratories by a suitable instrumental interface to a time-shared computer. In principle, even very complex samples can be analyzed on a routine basis. However, development of reproducible sampling, transfer, storage and desorbing procedures is essential for such analyses.

Techniques presently available for analysis of volatile organic components of body fluids are based on extraction with a suitable solvent, distillation, headspace gas technique, and, in the case of solids, direct head adsorption. Headspace gas techniques are a true representation of volatile material, since each component present in a liquid characteristically contributes to the total headspace gas according to its own vapor pressure at a given temperature. In terms of speed, reproducibility, and true volatile composition, this technique is superior to the others.

Since biological, air, and water samples often contain very complex volatiles consisting often of several hundred compounds, high resolution open tubular capillary columns are very useful; although conventional packed columns may also be used for certain analyses. To make full use of the potentials of high resolution capillary columns, the gas sample should be introduced as a sharply defined plug. Unfortunately, where the sample contains only trace quantities of organic volatiles, the sensitivity of detectors presently available for this kind of analysis falls short by several orders of magnitude, unless volatiles are concentrated. This is true in the case of volatile organic compounds in air and tobacco smoke and in the headgases of petroleum, water, foods, beverages, tissue cultures, and the body fluids.

Previous methods for concentrating traces of organic volatiles include the use of cold traps, freezing out in short tubes, enrichment in relatively short pieces of capillaries or small bore packed columns directly attached to the injector port, and cryogenic injection directly into the capillary column. Freezing is less desirable for samples containing excess moisture, since the water would tend to remove the volatiles as it freezes out. Cryogenic injection is usable only for relatively concentrated samples because the total volume of the sample including the water must pass through the system at a relatively low flow rate.

There has been a need for a relatively simple, fast, inexpensive and reproducible method for detecting diseases, determining the progress of disease, and measuring effectiveness of treatment of disease in humans and animals, particularly a method that lends itself to massive screening for disease.

There has also been a need for a relatively simple, fast and reproducible method for analyzing organic volatiles in closed environments, such as spacecraft, submarines, high altitude airplanes and other enclosures.

A further need is sampling and analysis for forensic purposes, such as identification of objects, marking or providing a "signature" to products by adding some compounds, which cannot be masked from detection.

Air pollution presents additional needs. At the present time, transportation largely depends on vehicles using combustion engines which emit large amounts of substances in the air which effect human environments. Low molecular weight olefins and aromatics in automobile emissions are known to participate in the petrochemical formation of smog. The high molecular weight end of the spectrum of substances emitted are potentially harmful compounds, such as polynuclear aromatic hydrocarbons and heterocyclic compounds, some of which are known to be potent carcinogens.

The majority of people living in industrialized areas are forced to inhale many of these substances daily in varying amounts and changing composition. It has been established that air pollution in general is responsible for a wide variety of pathological conditions involving the respiratory tract, and the pulmonary system. Except for a few isolated cases, little is known about the nature of the chemicals responsible and no information is available on the synergistic and long-term effects.

Some of the reasons for the lack of data on volatile organic compounds in air are due to the difficulties encountered in sampling and analysis. Combustion processes are incomplete and lead to a variety of products of great complexity. Several hundred compounds, therefore, must be analyzed in concentration ranges which can differ by several orders of magnitude.

The problems in analysis of air are similar to the ones encountered for volatiles in body fluids; however, sampling requirements are different for air pollution. Besides fixed gases, water constitutes the major component of air. This leads to considerable difficulties of both sampling and analysis. The organic materials to be analyzed in air are present at a concentration level of 7 to 10 orders of magnitude lower than water. These facts have hindered successful analysis with prior art techniques.

In general, the same problems exist in sampling and analysis of organic compounds in petroleum exploration, water pollution, flavor and aroma analyses, tobacco smoke analyses, and the like. In this connection there is a need for sampling, transfer, storage and analysis which lends itself to the detection of ultratrace quantities of volatiles, such as sampling at a remote place and bringing back a small enriched sample for analysis at a central location.

Some desirable features of a good sampling and analysis system are (1) enriched concentration of volatiles from a large sample, for example air, with minimum interference of moisture, (2) complete collection in the volatility range considered, (3) ability to simultaneously collect multiple samples, (4) storage and transportation of sample without loss or change in composition for analysis at a later time, and (5) quantitative and unaltered regeneration at time of analysis.

In order to be useful for practical applications in an average laboratory, the sampling procedure should also allow samples to be taken with a minimum of interference; the speed of sampling should be sufficient to follow rapid compositional changes; regeneration should be done without intermediary steps, such as extraction; and ordinary laboratory personnel should be able to handle the collection or sampling apparatus.

Presently available sampling technology include cryogenic techniques; at subambient temperatures with solid adsorbents, or conventional gas-liquid chromatography (GLC) packings; at room temperature with solid adsorbents or conventional GLC packings with heat desorption; and at room temperature with solid or chemically bonded stationery phases to adsorbents with liquid extraction. While these sampling techniques do have certain advantages, they do not have all of the desirable features previously mentioned. For example, in cryogenic sampling techniques, there are difficulties in regenerating the sample, especially for high molecular weight compounds. Also, there is strong interference by excess water; it is relatively expensive; and there are losses due to fog formation. With adsorbents at subambient temperatures there is interference from water, the sample size is limited (depending upon the adsorbent) recovery is incomplete, there are viscosity problems with GLC packing, and artifacts are quite common. With adsorbents at room temperature there is a loss of low molecular weight compounds to various degrees (depending on the nature of the adsorbent), recovery is incomplete (depending on the adsorbent), surface reactions are more likely than with many other techniques, excessive heat is necessary for very active adsorbents, flow rate is restricted especially with GLC packings, and there are decreasing efficiencies of recovery with high molecular weight compounds. With sampling techniques utilizing adsorbents at room temperatures, much time is consumed, the sample is diluted with extractant (which is difficult to remove without loss), secondary reactions are possible, skill is required and automation is difficult.

Porous polymers used as adsorbents prior to the present invention were not entirely satisfactory. For example, a porous polymer of styrene and divinylbenzene, sold under the trademark Porapak P, was limited to 230° C. for desorption, and at 200° C. the bleed from this adsorbent was considerable, producing artifacts during analysis. The desorption temperature limit prevents effective desorption of higher molecular weight volatile organics.

Another adsorbent used is a carbon molecular sieve (Carbosieve) prepared by thermally cracking polyvinylidene chloride. It has great surface area and high temperature stability; however, temperatures well over 400° C. are needed to desorb organic volaties, which causes pyrolysis of some of the compounds. Also, extreme care must be taken in its regeneration, handling, and storage.

Another adsorbent used is activated charcoal; however, many of the adsorbed volatiles are difficult to recover because of irreversible adsorption and surface reactions.

In prior art analyses, samples are customarily desorbed prior to injection into the chromatograph, and it is necessary to utilize syringe injections with their attendant disadvantages.

In prior art chromatographs it was customay to use open tubular columns, as disclosed by M. J. E. Golay in U.S. Pat. No. 2,920,478, Jan. 12, 1960. The majority of all open columns is made of stainless steel, although glass is sometimes preferred because of the reaction of stainless steel with labile organic compounds. However, there are many problems in the fabrication and handling of glass columns.

An adsorbent used in one aspect of the present invention is a polymer of 2,6-diphenyl-p-phenylene oxide (PPPO) sold commercially under the registered trademark TENAX GC. This polymer was developed by AKZO, Research and Engineering N.V., Arnhem, The Netherlands. Technical Bulletin No. 24 of Applied Science Laboratories, Inc., State College, PA., the United States distributor, states that the polymer is useful as a polymer column packing material for the separation of high boiling polar compounds such as alcohols, polyethylene glycol compounds, diols, phenols, mono and diamines, ethanolamines, amides, aldehydes, and ketones. Several articles on this porous polymer by R. Van Wijk, of AKZO, supra, relate to its use as a column packing material and various applications in gas chromatography. However, prior to this invention Tenax GC was never used or even suggested for use as an adsorbent for the collection and desorption of volatile organic compounds.

SUMMARY OF THE INVENTION

This invention is directed to an improved system for reproducibly analyzing, both qualitatively and quantitatively, trace amounts of a large number of organic volatile compounds.

The system includes an improved sample trap for collecting and enriching a sample of volatile organic compounds existing in a gaseous medium or in the headspace gas of a fluid or solid medium. The sample trap with its enriched organic volatiles may be easily transported to a different location for analysis or stored for later analysis. The sample trap is incorporated as an insert in a novel injector port of a gas chromatograph (GC), whereby the entrapped organic volatiles are directly injected into a GC precolumn maintained at cryogenic temperature to form a sharply defined plug. The system also includes a novel capillary separating column which has efficiencies in separations of about twice that of comparable stainless steel capillary columns. The system is compatible with commercial gas chromatographs and the various detectors therefor.

Applications of the system include (1) analyzing the headspace gas of body fluids and comparing a profile of the organic volatiles with standard profiles for the detection and monitoring of metabolic disorders, (2) analyzing the headspace gas of foods, beverages, and tobacco products and comparing a profile of the organic volatiles thereof with reference profiles so that quality, flavor and aroma can be monitored, controlled and studied, (3) similar analysis for determining the organic pollutants in samples of water and air to monitor and control pollution, (4) analysis of headspace gas of cores to assist in determining the existence of petroleum, (5) adding a specific set of organic compounds to a product to provide it with an identifiable signature.

The sample trap contains as an adsorbent, a porous polymer of 2,6-diphenyl-p-phenylene oxide (TENAX GC). It has been found that this porous polymer may be used for concentrating atmospheric, gaseous, or aqueous volatile organic compounds in the range, $C_3-C_{15}$ at ambient temperature (20–1000 ml/min flow). All hydrocarbons other than methane may be concentrated if the sample trap is cooled (−80° C). The adsorbent has temperature stability up to 400° C. It is inert to the entrapped volatiles and will desorb them below the range of pyrolysis. It has also been found that the sample trap may be transported or stored without deterioration of the entrapped volatiles. Also, the adsorbent may be regenerated for subsequent reuse.

The novel injector port has a hollow body which receives the sample trap as an insert in a sealed relation. The injector port fits into the GC injector port heater and flow of carrier gas during desorption is through the sample trap.

The novel capillary separating column is formed of nickel which has been etched to provide increased and uniform surface area.

Improved techniques and means for reproducibly analyzing, both qualitatively and quantitatively, trace amounts of a large number of organic volatiles are provided. The system fully meets the requirements for the sampling and analyses system previously set forth, and numerous applications for gas chromatography, previously impractical, are also set forth.

DESCRIPTION OF PRESENTLY PREFERRED EMBODIMENTS

In one aspect of the invention, volatile organic compounds from a sample are adsorbed on a porous polymer based on 2,6-diphenyl-p-phenylene oxide (PPPO) and are desorbed at temperatures from ambient up to temperatures of the order of 400° C. depending upon the particular volatile organic compound. The adsorbent should have the following properties: (1) high affinity for volatile organic compounds, (2) hydrophobicity, (3) temperature stability up to 400° C., (4) good desorptivity and (5) relative inertness to the sample. It is also desirable that the adsorbent can be regenerated. The porous polymer of PPPO has efficient adsorptivity and desorptivity, and it can sustain the relatively high temperatures previously mentioned. PPPO may be prepared as taught in U.S. Pat. No. 3,432,466. The porous polymer is a poly-paraphenylene oxide, substituted with phenyl groups on the 2 and 6 positions of the aromatic unit as shown in the formula below:

The material is a high molecular weight (0.5 – 1 × 10$^6$) linear polymer, soluble in, for example, lower chlorinated hydrocarbons, tetrahydrofuran, carbon disulphide, dioxane, pyridine, and cyclohexannone. It is not soluble, however, in alkanes, n-prophylchloride and higher homologues, cyclohexane, alcohols, acetone, diethylether, ethylacetate, etc.

A further description of this polymer is contained in "High Temperature (Over 400° C.) Resistant Polymeric Column Packing Material" by R. van Wijk, Chimia, Vol. 24, pp. 254–56, 1970, and "The Use of Poly-para-2,6-diphenylphenylene Oxide as a Porous Polymer in Gas Chromatography" by R. van Wijk, Journal of Chromatographic Science, July, 1970, pp. 418–420.

This porous polymer is marketed under the U.S. registered trademark TENAX GC. It was developed by AKZO N.V. at Arnhem, The Netherlands, and is marketed by Enka N. V. of The Netherlands. Technical Bulletin No. 24 of Applied Science Laboratories, Inc., State College, Pa., sets out properties of this porous polymer as being suitable for the separation of high boiling polar compounds. As previously mentioned, this porous polymer has never been suggested for use or used as an adsorbent for volatile organic compounds before the present invention.

PPPO, made in accordance with U.S. Pat. No. 3,432,466 is further processed as follows to form TENAX GC: PPPO is dissolved in a suitable solvent, the PPPO in solution precipitates in a partly crystalline state, the precipitate formed is isolated, washed, and subsequently subjected to a heat treatment.

More particularly, amorphous PPPO is dissolved in a particular solvent in which amorphous PPPO is moderately soluble but in which crystalline PPPO is not soluble, for instance: benzene or dimethyl formamide. The polymer is caused to precipitate out while in a substantially crystalline form. This may be achieved, for example, by keeping the solution at room temperature (about 40° C.) for about 20 hours. The resulting precipitate is isolated and dried in vacuo for approximately 12 hours at about 100° C. The dried material is subsequently subjected to a heat treatment in vacuo, or, in an inert medium such as nitrogen. This heat treatment may be carried out at 300° to 400° C., by preference at 350° to 370° C. the duration of the heat treatment is at least 2 hours. During the treatment recrystallization takes place.

The degree of crystallinity is determined by the duration and the temperature of the heat treatment. It is preferred to use materials which contain 10 to 45%, preferably 20 to 30%, crystalline PPPO. Subsequently, the material obtained is preferably ground and grouped into various mesh sizes. Finally, the material thus obtained is heated for at least 1 hour in vacuo at 300° –400° C.

The advantages of TENAX-GC over other materials tried for trapping are more efficient adsorption of volatiles at room temperature and more efficient desorption of the same materials at 300° C., a temperature that TENAX-GC can easily withstand. The stability of volatile organics trapped on the TENAX-GC is very high, and trapped samples can easily be stored or shipped to another laboratory for analysis. Reproducibility of results is excellent. It is also found that the volatiles from a single urine sample can be collected in multiple parallel TENAX-GC traps and reproducible GC results obtained. This allows GC analysis of volatiles from the same urine sample with a flame ionization detector, a flame photometric detector, and GC/MS. It has also been found that volatiles collected in the TENAX-GC traps can be stored for at least two weeks without deterioration of the entrapped volatiles. Traps stored at 0° C., 4° C., and room temperature give reproducible GC results.

The volatile organic compounds may be adsorbed by the porous polymer from gas samples and from liquids and solids after suitable volatilization, such as by heating.

Volatiles from solids and liquids are first passed through a water condenser and then are swept past the porous polymer adsorbent by a suitable inert carrier gas, such as helium, nitrogen, and the like. Gas samples, such as air and breath samples, are pulled by a vacuum through the condenser and then past the adsorbent. The volatiles are adsorbed by the adsorbent which advantageously may be maintained at room temperature.

The adsorbent may be used for concentrating atmospheric, gaseous, or aqueous volatile organic compounds in the range $C_3$–$C_{15}$ at ambient temperature (20–1000 ml/min flows). All hydrocarbons other than methane may be concentrated if the adsorbent is cooled (−80° C.). In order to prevent moisture uptake, a cooled condenser (4° C.) should precede.

It has been found that the organic volatiles obtained by using TENAX-GC are enriched due to the fact that TENAX-GC adsorbs the organic volatiles as the stream passes through.

The adsorbed volatiles are then desorbed from the adsorbent, preferably at temperatures from 230°–300° C. for volatiles from body fluid samples and most other volatiles, although temperatures up to 400° C. for short periods of time may be used.

The organic volatiles are collected and then the sample trap is either stored, transported or the volatiles desorbed in an analytical instrument, for example, to the precolumn of a gas chromatograph. When the volatiles are transferred to the separating column, analysis is started at a given temperature. The temperature may be increased as is customary in gas chromatography. A mass spectrometer can be used as a specific detector for the gas chromatograph and profiles or fingerprints of the volatile organic compounds are readily obtained. Also, flame photometric detectors and other selective or specific detectors may be used for determining compounds containing sulfur, phosphorous, nitrogen, metals, etc. Flame ionization detectors may be used for total organic profiles, an infrared spectroscopy, ultra violet spectroscopy, nuclear magnetic resonance, neutron activation analysis, fluorescence spectometry and the like may be used.

Multiple sampling is possible by placing several traps containing the porous polymer in parallel, for example, when sulfur compound detection and GC/MS data are required, in addition to flame ionization profiles.

Figure 1:
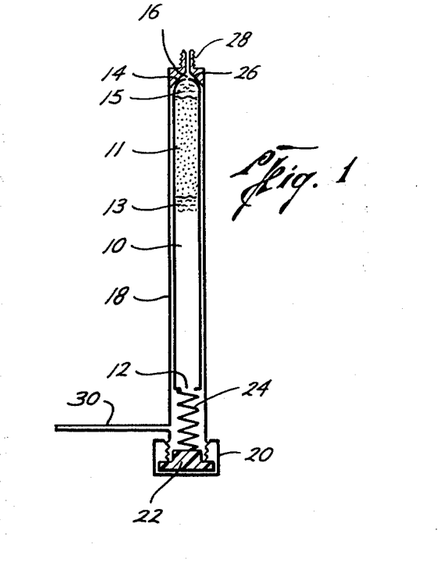
FIG. 1 is an elevational view, in section, illustrating an injector port with a sample trap-insert according to the invention.

As previously mentioned, in order to achieve reproducible results and, at the same time, provide convenient methods of sampling, transfer, storage, and analysis, a sample trap which ultimately becomes an insert for a modified injector port was developed, both of which are illustrated in FIG. 1, to which reference is now made.

The sampling trap includes an elongated test tube like body 10 which is open at one end 12 and tapered at the other end 14 which is provided with a small opening 16. The sample trap body 10 is a glass tube containing an adsorbent 11, preferably TENAX-GC, 35/60 mesh, and silanized glass wool 13 and 15 which is placed at each end of adsorbent 11 to hold it in place. Good results have been obtained by utilizing a glass tube 10 of 11 cm × 8 mm ID × 10 mm OD containing 2 ml adsorbent. The adsorbent is first preconditioned with helium flow at 375° C. for 30 minutes.

The adsorbent in the sample trap may be regenerated by heating the sample traps in a brass block at approximately 375° C. for 30–45 minutes while purging with a flow of helium of 30ml/min. Once the traps have been reconditioned, they may be stored for future use in Teflon lined screw capped containers.

The injector port includes a tube-like body 18 which is closed at one end by a removable closure 20 which includes a Teflon insert 22. A spring 24 is provided which engages the plug 22 and open end 12 of sample trap body 10 yieldingly urging tapered surface 14 into sealing engagement with a mating internally tapered surface 26 of body 18. The tapered surfaces 14 and 26 are mating surfaces to provide an effective seal between the sample trap and injector port whereby flow through the injector port must flow through adsorbent 11. End 26 of injector port body 18 is provided with an externally threaded port 28 for connection to a gas analyzer, for example, to a precolumn inlet of a gas chormatograph, see FIG. 4.

Injector port body 18 is provided with an inlet port 30 adjacent to end 12 for flow of an inert purging gas, such as helium, nitrogen and the like through the sample trap for desorbing the entrapped organic volatile compounds from the adsorbent.

Figure 2:
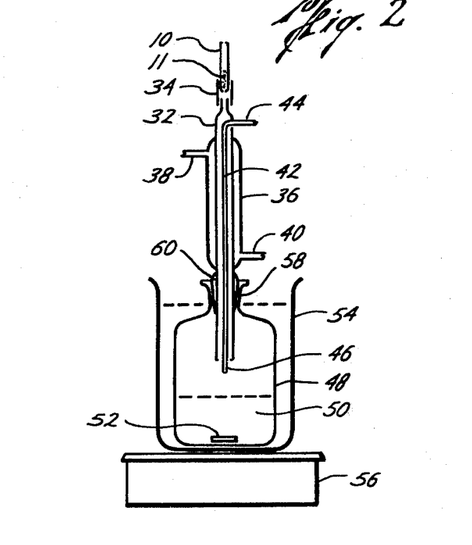
FIG. 2 is an elevational view, in section, of an aqueous volatile sampler using the sample trap-insert of FIG. 1.

Referring now to FIG. 2, the sample trap is illustrated in conjunction with an aqueous volatile sampler for liquids. The volatile sampler includes a condenser body 32, the upper end of which is secured to the sample trap by means of a suitably inert sleeve 34, of Teflon or a standard tapered joint. The condenser body 32 is surrounded by an elongate tubular chamber 36 which is provided with inlet and outlets 38 and 40 for circulating a suitable coolant, such as chilled water. A central tube 42 having an inlet 44 and an outlet 46 is provided in condenser body 32 for circulation of a suitable purging gas, such as helium, nitrogen and the like. The condenser body 32 is fitted into a container 48, containing the sample 50 to be analyzed, and a magnetic stirring bar 52. The container 48 is placed in a water bath 54 disposed upon a heating element 56.

The container 48 has an internally tapered joint 58 to receive a mating externally tapered joint 60 at the lower portion of condenser body 32 to provide a seal between condenser body 32 and container 48.

In using the aqueous volatile sample of FIG. 2, a liquid sample, for example, 10–200 ml urine, is placed in container 48 disposed within water bath 54. The urine sample is heated to 80°–90° C. and is stirred with the magnetic stirring bar. Helium flow through central tube 42 is adjusted to 15–20 ml/min and the organic volatile compounds are purged and dried while passing through condenser body 32. The adsorbent 11 in the sample trap adsorbs the volatile organic compounds from urine sample 50. After the sample has been purged for about one hour, the sample trap is removed from the condenser and is placed into the injector port as illustrated in FIG. 1. If the sample is to be desorbed and analyzed immediately, the outlet port 28 is secured to a GC precolumn inlet, as presently to be described. If the adsorbed sample is to be stored or transported, the sample trap is placed in a closed container.

While only one sample trap is illustrated in the aqueous volatile sampler of FIG. 2, several sample traps may be manifolded in parallel, when multiple samples are required or desired.

Volatiles from solid samples are obtained in substantially the same manner with the aqueous volatile sampler of FIG. 2, by placing the solid sample, such as oil well cuttings, cores and the like in container 48 and operating the sample as described for liquid samples.

Advantageously, headspace gas technique is used in adsorbing the organic volatiles thus insuring truly representative mixtures of organic volatiles. In previous methods, not as many organic volatile compounds are split out in one run and there is selective interaction of solvent with the sample constituents in liquid-solvent extraction.

Figure 3:
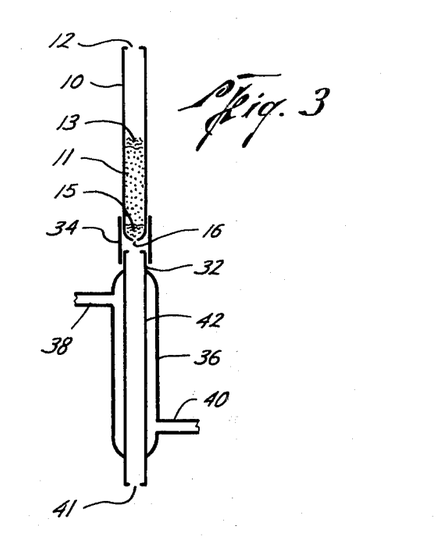
FIG. 3 is an elevational view, in section, illustrating an air-breath sampler using the trap-insert of FIG. 1.

Referring now to FIG. 3, a gas sampler, such as an air or human breath sampler, is illustrated. This sampler is generally similar to the aqueous volatile sampler of FIG. 2. For ease of reference, the same reference numerals are used to designate like or corresponding parts in FIGS. 1 and 2. In this gas sampler, the sample trap is secured to the condenser as in FIG. 2 and chilled water is circulated about the body 32. In the case of breath analysis, the subject exhales into an inlet 41 while vacuum is applied to end 12 of the sample trap. Satisfactory results have been obtained with a vacuum of 0.5–2 liters/min. The breath introduced into inlet 41 of condenser body 32 is drawn through condenser body 32 and dried and then past adsorbent 11. For breath samples, about 50 exhalations have been found to provide having a sufficient sample adsorbed by the adsorbent. Air is introduced into the system in the same manner for a suitable period of time, for example, 1 hour.

In all cases after the organic volatiles are collected, the sample trap may be placed in a container and transported to a central location for later analysis. It has been found that the sample trap may be stored indefinitely without deterioration of the entrapped organic volatiles.

Preferably, the adsorbent is TENAX-GC. However, other adsorbents may be used in the novel insert trap depending upon the analysis desired. For example, any styrene-divinylbenzene polymer, activated charcoal, carbonmolecular sieve or polymer of sufficient surface area may be used for special analysis.

Figure 4:
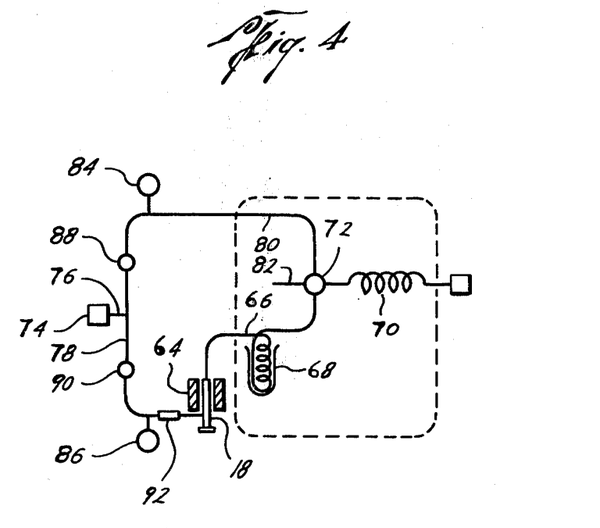
FIG. 4 is a schematic view illustrating a gas chromatograph and injector port of FIG. 1 connected to a precolumn of the gas chromatograph.

Referring now to FIG. 4, a sample analysis and transfer system is illustrated. The injector port with the sample trap containing the adsorbed sample, as illustrated in FIG. 1, is inserted into an injector port heater 64 and the outlet end 28 of the injector port is attached to a precolumn 66 extending in a coiled manner through a container 68 containing dry ice or liquid nitrogen, (not shown) whereby a small "plug" of the desorbed organic volatiles is formed. The precolumn is attached to a gas chromatograph separating column 70 by means of a four port valve 72 (Valco, Inc., Houston, TX.). As described later, temperature programming is used in this mode.

A source of carrier gas 74 such as helium is connected by a flow line 76 to a first flow line 78, which is connected to inlet port 30 (see FIG. 1) of the injector port. A second flow line 80 is connected to four port valve 72, which is connected to a vent line 82. Suitable pressure regulators 84 and 86, toggle switches 88 and 90, are provided in flow lines 60 and 58, respectively, and a rotameter 92 is provided in flow line 78.

The precolumn 66 can be coated with the same phase as is the gas chromatograph separating column 70, coated with another phase or be uncoated.

The purpose of four port valve 72 is to allow a dual carrier flow, one through the sample trap and precolumn 66, preferably at 20 ml/min., and another constant carrier flow through separating column 70, preferably at 3 ml/min.

While the sample is being transferred to precolumn 66, the carrier gas flowing through precolumn 66 is vented through vent 82, and at the same time there is a constant flow through separating column 70 through line 80 under pressures controlled by pressure regulator 84. The heater 64 is adjusted to the desired temperature, for example, 230°–300° C. although ambient or temperatures of the order of 400° c. may be used for certain analyses, as previously mentioned. The carrier gas flowing in line 78, as regulated by pressure regulator 80, carries the desorbed volatiles from the adsorbent whereby the adsorbed volatile organic compounds are transferred from the sample trap to precolumn 66 which is cooled with dry ice in container 68.

With the volatile sample now transferred to precolumn 66, four port valve 72 is rotated 90° and the sample in the precolumn is transferred to the separating column for analysis in the manner of a syringe injection, as previously described, and the carrier gas in line 80 is vented out vent 82.

Chromatography is begun when the sharply defined plug or organic volatiles is transferred to separating column 70.

In the sample transfer and analysis of the following examples, the precolumn was 10 feet long and 0.04 in. ID and was coated with the same liquid phase as the separating column 70 which was 300 feet long and 0.02 in. ID nickel column specially prepared by etching with an acid solution. A 600-foot column was used in air sample analysis.

Stainless steel is predominately used for capillary separating columns, but because of its reaction with the labile organic compounds, glass (silanized) is sometimes preferred. Since glass capillary columns as yet are neither suitable nor stable for routine analysis, a compromise was made in the choice of material. Nickel 200 (0.032 inch O.D. × 0.02 inch in ID; Handy and Harmon Tube Company, Norristown, Pa., thin walled capillary columns were chosen.

In order to increase the efficiency of the nickel columns, a mild etching procedure was established to provide increased and uniform surface area for the liquid phase.

Concentrated nitric and acetic acids are mixed with distilled water (1:1:1) as a stock solution. The stock solution is diluted with distilled water (1:1) and is passed through the column (14 psi pressure). When the solution begins to pass through the column, the pressure is released and the column, now containing the etching solution, is allowed to stand at room temperature for 1 hour. The column is then washed with 5 volumes of distilled water and dried with acetone. These columns have efficiencies about twice that of comparable steel columns.

The polar liquid phase material chosen was Emulphor-O, a polyoxyethyleneglycol etherified with octadecanol because of its relatively high polarity and temperature stability (200° C.). A 7–10% solution in chloroform was prepared. A volume of 5–7 ml. of the coating solution was measured into a vessel, which was then pressurized to 3–6 psig. The end of the column was dipped into a small beaker filled with water. The pressure was adjusted to give a small air bubble every 1–2 seconds. Coating took approximately 5–8 hours. The carrier gas was continued for an additional several hours, then another charge of approximately 0.5 ml. was again passed through the column under the same speed. The pressure was increased stepwise to about 15 psig for the second coating which was allowed to dry for another 6 hours.

For conditioning, the column was placed in a gas chromatograph and carrier gas of 10 psig was allowed to flow for 1 hour in the same direction of flow as when coating. The temperature was then raised slowly at the rate of 0.5° C/min. up to approximately 30° C. below the temperature limit of the phase. After 2 hours, the temperature was raised again at the same rate to the temperature limit of the phase and maintained for 2 days.

Other phase materials may be used as coatings and preparation of other columns may be used. For a more detailed description of preparation of open tubular columns for chromatography, reference is made to "Preparation of High Resolution Nickel Open Tubular Columns" by A. Zlatkis, et al. in Chromatographia, March, 1974.

While any desired chromatograph and ancillary analyzers may be utilized, in the following examples, a Perkin-Elmer 900 Gas Chromatograph with flame ionization detectors (FID) and a Model 9000 gas chromatograph-mass spectometer GLC MS (LKB -Producter AB, S161 Bromma 1, Sweden) were employed. The sample trap was inserted into the injector port which was in turn inserted into an injector heater, held at a temperature of 300° C. The volatiles were desorbed from the adsorbent with helium at a flow rate of 20 ml/min and trapped on the precolumn by the four port valve.

After a trapping period of 20 minutes with dry ice as the coolant, the container was removed. Programmed temperature GLC commenced at room temperature for 15 minutes; with the flow rate of carrier gas (helium) at 3ml/min. After 15 minutes the column temperature was raised to 80° C. and held for 15 minutes, then programmed up to 190° C. at 2°/min. (0.5°/min. for air samples). Hydrogen and air flows for the FID were adjusted to 14 and 50 psig, respectively.

The sampling, transferring, collecting and analyzing of volatile organic compounds from samples require less than 4 hours total. They required only 1.5 hours of sampling handling, 1 hour sampling and ½ hour transfer, and less than 2½hours of analysis. The time factor for analysis is, of course, variable, but of critical importance is the time of sampling. As previously mentioned, the number of samples that can be trapped is limited only by the number of sampling systems and/or manifolds of the system that are available. This is significant since the trapped samples may be conveniently stored. Storing sample traps with their trapped enriched organic volatiles is much easier and desirable than storing aqueous samples. This feature allows samples previously extracted to be either stored or shipped to another laboratory for analysis. Significantly, not only can specific volatile organic compounds be identified, but the quantity of each organic volatile compound present can be determined, provided the quantity of the original sample is known.

The following examples illustrate typical applications of the invention.

EXAMPLE 1

In this example urine samples from a normal human being and a diabetic human being were analyzed and compared. 100 ml of each of the samples was placed in the container 48 of a 100° C. water bath 54 as illustrated in FIG. 2. The surfaces of the samples were continuously swept with helium through the tube 42 at 20 ml/min. The volatiles were passed through the condenser body 32 and dried, and then trapped onto the adsorbent 11, in the sample trap. In order to increase volatilization, 30 g of $(NH_4)_2SO_4$ for 100 ml urine was added.

After a period of about 1 hour, the adsorbing was stopped, and the sample trap was removed from the condenser 32 and placed in the injector port as illustrated in FIG. 1, which was in turn placed in the injector heater of the gas chromatograph, see FIG. 4. The sample was then eluted at 300° C. and 20 ml/min. into the precolumn located in dry ice, for a period of about ½ hour. The four port valve was then rotated and the sample was transferred into the separating column and the chromatographic profiles illustrated in FIG. 5 were obtained. It is noted that there is a striking visual difference between the chromatographic profiles of the urine sample of a normal or healthy human being and that of the diabetic.

The volatile organic compounds in normal human urine are numbered on the chromatographic profile and are set forth with the same numbering in the following Table I.

EXAMPLE 2

Figure 6:
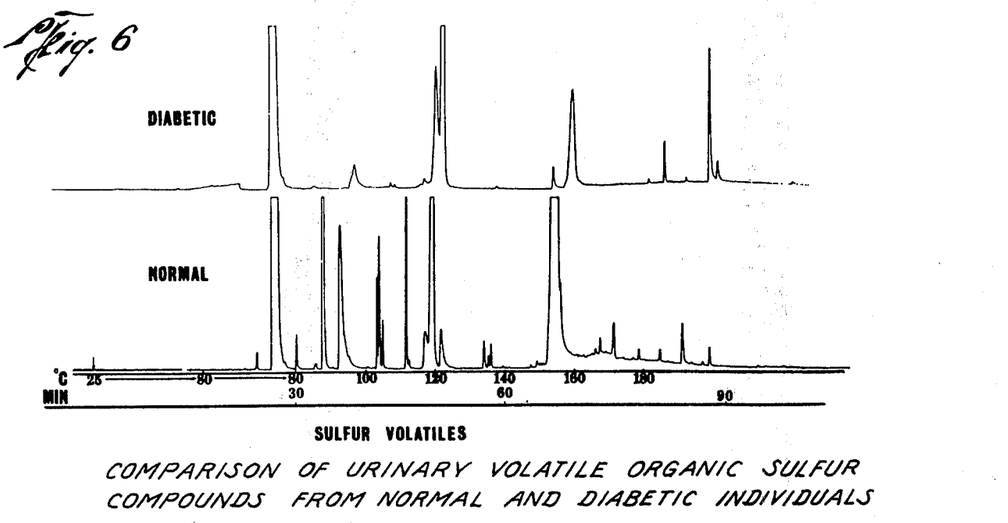
FIG. 6 is a pair of chromatographic profiles comparing urinary volatile organic sulfur compounds from normal and diabetic individuals.

In this example the urine samples of Example 1 were analyzed with a Shimadzu Model GC-58P Gas Chromatograph with a flame ionization detector (FID) for obtaining sulfur chromatographic profiles. The sulfur chromatographic profiles of normal and diabetic urine are illustrated in FIG. 6 to which reference is made.

Again, there is a striking visual difference between the urinary volatile organic sulfur compounds from normal and diabetic individuals.

It was found that urine samples taken 8 days apart, and samples which were taken and stored for periods of time, provided similar or reproducible profiles. The samples in Examples 1 and 2 were taken as multiple samples at the same time.

Although the variance between the urinary profiles of different individuals is significant, the profile for the

Table I

| Volatile Organic Compounds in Normal Human Urine | | | |
|---|---|---|---|
| PeaK No.[a] | Compound | Peak No.[a] | Compound |
|  | Acetone |  | $C_1$-Furan |
|  |  |  | Thiolan-2-one (tent.) |
| 1 | 2-Butanone |  |  |
|  |  | 13 | 2-Heptanone[b] |
| 2 | Ethanol |  | 3-Methylcyclopentanone[b] |
|  | Propionaldehyde |  | G(?)-Methyl-3-heptanone |
| 3 | 3-Methyl-2-butanone[b] |  | 3-Octanone[b] |
|  | 2,3-Butanedione |  | Methylpyrazine |
|  | 2,3-Dimethylfuran[b] |  | 2-n-Pentylfuran[b] |
|  |  |  | 2,6- or 2,5-Dimethylpyrazine |
| 4 | 2-Pentanone[b] |  | Allylisothiocyanate[b] |
| 5 | 2,4-Dimethylfuran[b] |  | 2,3-Dimethylpyrazine |
|  | Chloroform |  | Furfural[b] |
|  | 4-Methyl-2-pentanone[b] |  | 2,3,5-Trimethylpyrazine |
|  | 3-Methyl-2-pentanone[b] |  | Vinylpyrazine |
|  | 2(?)-Methyl-5(?)-ethylfuran[b] |  | 2-Methyl-6-ethylpyrazine |
|  | Toluene | 14 | Pyrrole[b] |
| 6 | Dimethyldisulfide[b] |  | 2-Nonanone |
|  | 3-Hexanone[b] |  | Acetylfuran |
|  |  |  | p-Methylpropenylbenzene |
| 7 | 2,3,5-Trimethylfuran[b] |  | (tent.) |
| 8 | 5-Methyl-3-hexanone;[b] | 15 | Benzaldehyde[b] |
| 9 | 3-Penten-2-one[b] |  | β-Pinene (tent.) |
|  |  |  | 2-Methyl-6(?)-vinylpyrazine |
| 9 | 1-Methylpyrrole |  | 2-Methylpyrrole |
|  |  |  | Dimethylpyrrole |
| 10 | 4-Methyl-3-penten-2-one |  | 1-Butylpyrrole (tent.) |
|  | (tent.)[b] | 16 | Carvone[b] |
| 11 | 4-Butanol | 17 | Piperitone[b] |
| 12 | 4-Heptanone[b] |  | p-Cresol[b] |

[a]Peak numbers refer to numbers in FIG. 1. Identified compounds not numbered appear in the chromatograms between two numbered peaks in the order given in this Table. No numbers were assigned to these constituents because the experimental conditions for the GLC-MS analyses were different from the conditions for CLC analyses, with consequent slight changes in peak sizes and retention times.
"tent."=tentative.

Figure 5:
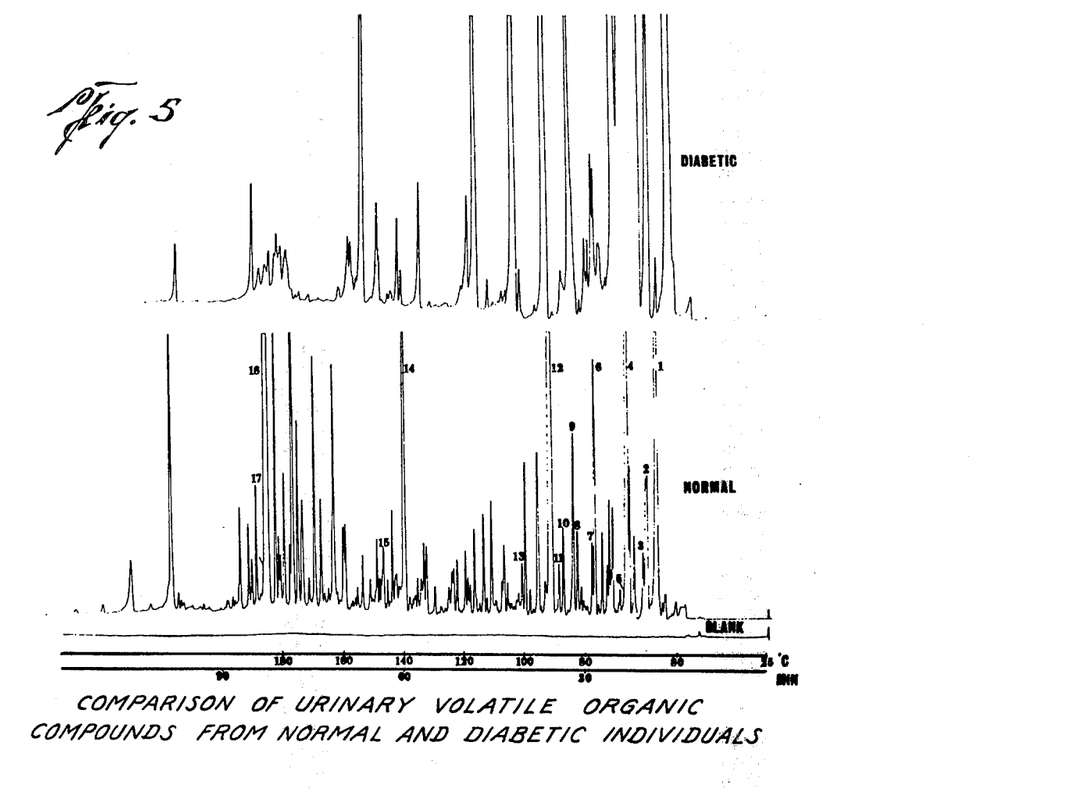
FIG. 5 is a pair of chromatographic profiles comparing uninary volatile organic compounds from normal and diabetic individuals.

In Table I, 51 compounds were identified by combined GC-MS (LKB 9,000), which compounds include ketones, alcohols, aldehydes, pyrroles, and pyrazines. While the chromatographic profile of the diabetic illustrated in FIG. 5 is typical, it has been found that different forms of diabetics have distinctly different profiles; however in general the profile of a diabetic has less components than a reference profile from a non-diabetic. Characteristic constituents in normal urines are 2-butanone, 2-pentanone, 4-heptanone, dimethyl disulfide, several alkyl furans, pyrrole, and carbone. In subjects with diabetes mellitus under insulin treatment, high concentrations of pyrazines, cyclohexanone, lower aliphatic alcohols, and octanals were found. In none of the normals or subjects with other diseases were the high concentrations of the above four groups of compounds found.

same individual remains remarkably constant on different days. Even though the profiles were compared over a period of two months involving dietary changes, no characteristic variations in the chromatograms were observed. The system lends itself to massive screening of persons for diabetes in that noninvasive samples, urine, may be taken, profiles made and compared to profiles of nondiabetic persons.

EXAMPLE 3

Figure 9:
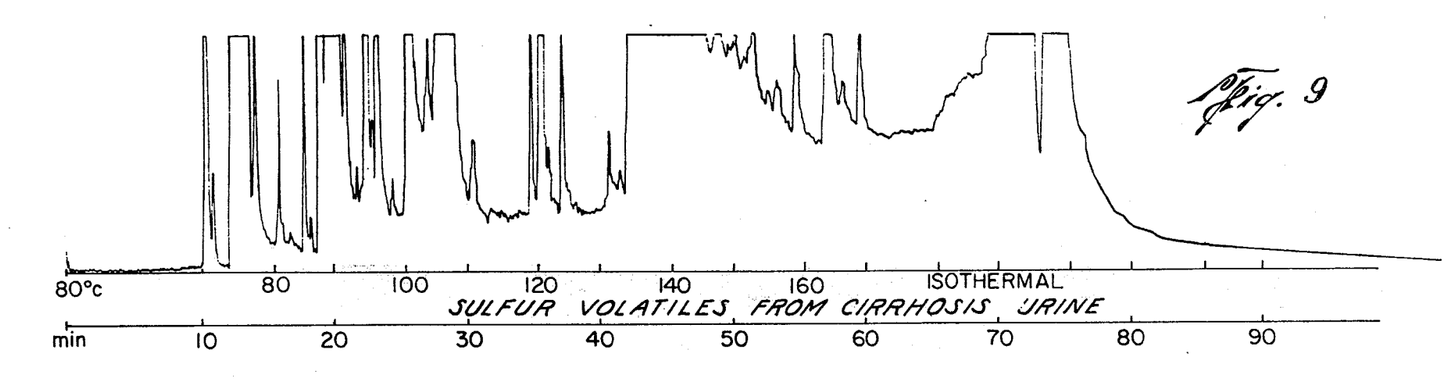
FIG. 9 is a profile of sulfur volatiles in urine from a person having cirrhosis of the liver.

In this example urine samples from a healthy or normal human being and one having cirrhosis of the liver were analyzed and chromatographic profiles were obtained as described in Examples 1 and 2. A sulfur profile of volatiles from a urine sample of a person having cirrhosis of the liver is illustrated in FIG. 9, which when compared to a sulfur profile of a normal person as illustrated in FIG. 6, shows striking differences. While the profile of the individual with cirrhosis of the liver has fewer overall components, it was found that it had more complex sulfur patterns. Thus, the method and system provide for the detection, the progress and the effect of treatment of cirrhosis of the liver by making profiles from time to time and comparing them to each other and to profiles of persons not afflicted with cirrhosis of the liver.

EXAMPLE 4

In this example urine samples from healthy or normal human beings and from schizophrenic patients were collected and analyzed as described in Examples 1 and 2. The chromatographic profiles of organic volatiles in samples from schizophrenic patients show differences from profiles of organic volatiles in samples from normal persons. Thus, detection and the progress of schizophrenic is possible by taking samples from time to time and comparing them to each other and to a normal profile.

EXAMPLE 5

In this example volatile organic compounds in normal human breath were analyzed. The subject exhaled through the inlet 41 of the air-breath sampler illustrated in FIG. 3 while a vacuum of 0.5–2 liters per minute was applied to the open end 12 of the sample trap. After about 50 exhalations, the sample trap was inserted into the injector port as illustrated in FIG. 1 and then the injector port was placed into the chromatograph illustrated in FIG. 4. About the only other change made in the procedure from that described in Examples 1 and 2 was that the adsorbent was increased to 7 ml and a wider trap was used for the cooling trap, which was changed from 0.02 in. to 0.03 in. ID.

Figure 7:
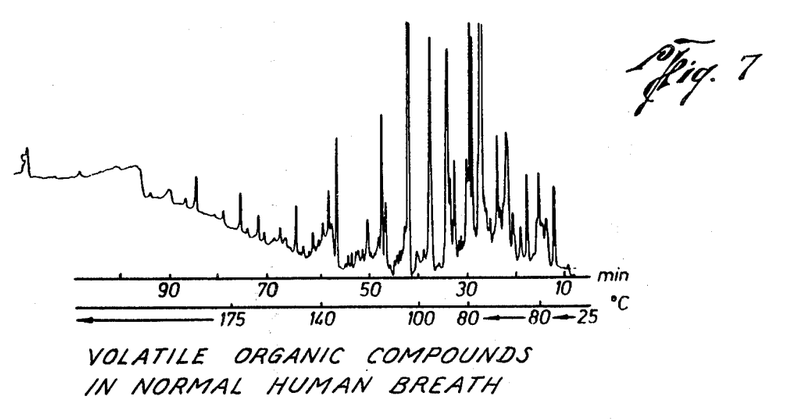
FIG. 7 is a profile of volatile organic compounds in normal human breath.

A chromatographic profile of volatile organic compounds in normal human breath was obtained and is illustrated in FIG. 7. A number of organic compounds have been reproducibly identified. These can be compared to chromatographic profiles of a subject's breath for the specific detection of volatile organic pollutants and their metabolites. Also, a direct correlation may be made with a specific pollutant profile of a given locale, such as illustrated in the following Example 6.

EXAMPLE 6

In this example samples of air were drawn through the air—breath sampler as illustrated in FIG. 3. Again, the only change made was an increase in the amount of the adsorbent for each sample trap, from 2 ml up to 7 ml and a wider flow was used for the cooling trap, which was changed from 0.02 inch to 0.03 inch ID. The transfer and analysis were the same as in the preceding examples.

For sampling inside a laboratory building, a vacuum source was readily available. For field analysis, the vacuum source consisted of a commercially available pump, portable generator, power supply and flow measuring and regulating devices were used.

More than 150 air samples were collected and analyzed over a period of 15 months under a variety of weather conditions. Samples were taken from varying locations in Houston, Texas, representing urban, industrial, and agricultural environments. Examples of urban locations are the campus of the University of Houston, located in the southeast part of the city, and four various downtown locations in the same city. Several petrochemical and plastic manufacturing companies in Pasadena, east of Houston, were chosen as representative for industrial environments, and a wooded section in the relatively unpopulated location, Lake Houston, approximately 30 miles north of Houston, was chosen as an example of the undisturbed environment.

Figure 8:
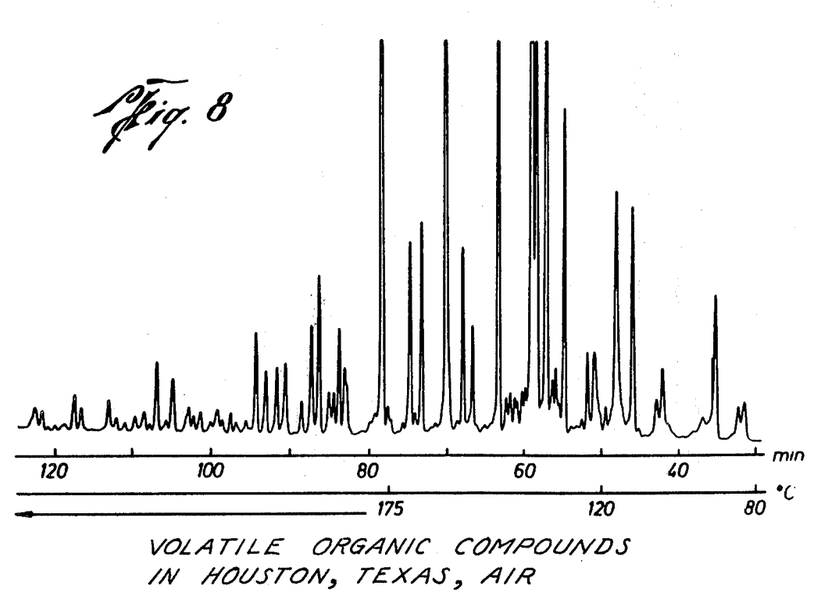
FIG. 8 is a profile of volatile organic compounds in the air in Houston, Tex., U.S.A.

The profiles obtained from urban environments were remarkably constant over the entire periods surveyed and only minor variances in composition were experienced. The total concentration of the volatiles, however, varied considerably. FIG. 8, to which reference is now made, shows a typical air sample, taken on the campus of the University of Houston. Approximately 100 substances, almost exclusively hydrocarbons, were identified and summarized. Alkanes represent the major part, especially at the low molecular weight end of the spectrum; whereas, substituted aromatics are more abundant for the high molecular weight end. All compounds eluting after benzene were well retained.

A number of profiles of air at different locations were made, but in order to shorten the disclosure, these profiles are not included. It was determined, however, that the concentration of volatiles in air not only depends on the sample location, but also is a strong function of the weather condition. For example, during the summer of 1973 a number of air stagnation periods led to severe conditions of smog. Samples taken during this time demonstrated the complexity of such a sample as a high concentration of volatiles. Sulfur profiles were obtained for a few samples and the same basic pattern could be observed for the sulfur compounds.

Striking similarities were found in the profiles of gasoline and air. Although intensities are different and the gasoline sample is more complex, the peaks are very similar. In the profiles of air taken close to the plastic manufacturing plant, many of the major components going into the plastics were readily recognized. The main differences were essentially limited to changes in the concentration of major components.

Accordingly, it is possible to determine with a degree of certainty the cause of air pollution and also to rapidly monitor the effectiveness of the control means.

EXAMPLE 7

In this example a sample of polluted water is placed in the container 48 of the aqueous volatile sampler of FIG. 2 and a sample of volatile organic compounds is adsorbed on the adsorbent in the sample trap insert. The sample trap is then placed in the injector port which, in turn, is connected to the precolumn 66 in the chromatograph illustrated in FIG. 4. The sampling can be at remote locations and small samples of water containing ultratrace quantities of volatiles may be sent to a convenient place for analysis, it being unnecessary to analyze the sample at the place where it was taken. The sampling, sample transfer and analysis are the same as described in Examples 1 and 2. Profiles obtained show numerous and trace amounts of volatile organic compounds as being present in the water, the profiles of which are not disclosed in order to shorten the disclosure. Additional profiles of polluted water are taken from time to time and during treatment in order to determine the effectiveness of treatment of the polluted waters.

EXAMPLE 8

Figure 10:
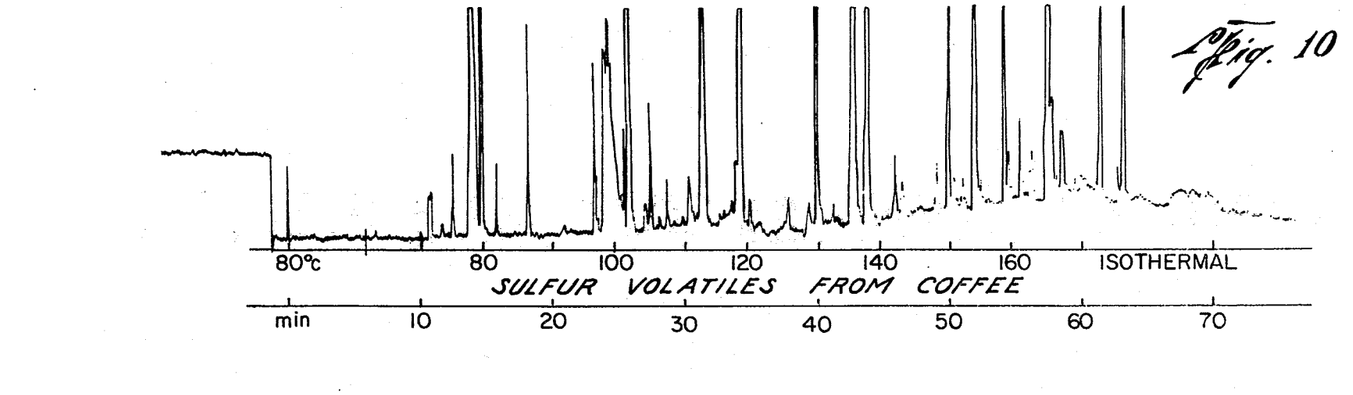
FIG. 10 is a profile of sulfur volatiles in coffee.

In this example flavor control of foods and beverages is illustrated. Profiles are made of samples of various foods and juices, for example, coffee, tea, tomato juice, apple juice, pineapple juice, orange juice, wine, maragarine, cheese, etc. These profiles are compared with profiles of a standard. This permits quality and flavor control to be obtained readily and easily by making suitable adjustments in the processing equipment. A sulfur profile of coffee is illustrated in FIG. 10, but profiles of other foods and juices are omitted to shorten the disclosure. It is significant, however, that using headspace gas adsorption according to the present invention a truly representative sample of the volatiles constituting the aroma is obtained and profiles made of it. Other methods, liquid-liquid extraction, liquid-solvent extraction and centrifuging do not obtain a truly representative sample of the volatiles. For example, there is selective interaction of the solvent with the sample constituents. With the present method specific volatiles constituting the product can be identified and quantitatively measured.

EXAMPLE 9

In this example samples of stack gases from refineries are analyzed. The apparatus and procedure were the same as that of Example 6. Profiles of these stack gas samples obtained provide identification of volatile organic compounds in the stack gases. Samples of these stack gases are taken after remedial steps to stop pollution by the stack gases and analyzed to determine the effectiveness of the remedial steps taken. These samples advantageously are taken at remote locations and then taken to convenient place for analysis. Thus, pollution by stack gases can be determined and steps taken to eliminate pollution.

EXAMPLE 10

In this example cuttings and cores from an oil well are placed in the container 48 of FIG. 2, the water bath 54 is heated to 100° C. and a sample obtained by adsorbing volatiles from the cuttings on the adsorbent in the sample trap insert, which is then inserted into the injector port, sample transfer and analysis made by the apparatus of FIG. 4 and as described in Examples 1 and 2. Profiles are obtained of the volatile organic compounds contained in the cuttings and cores which are readily identified and provides information as to whether a formation contains oil and gas.

EXAMPLE 11

Figure 11:
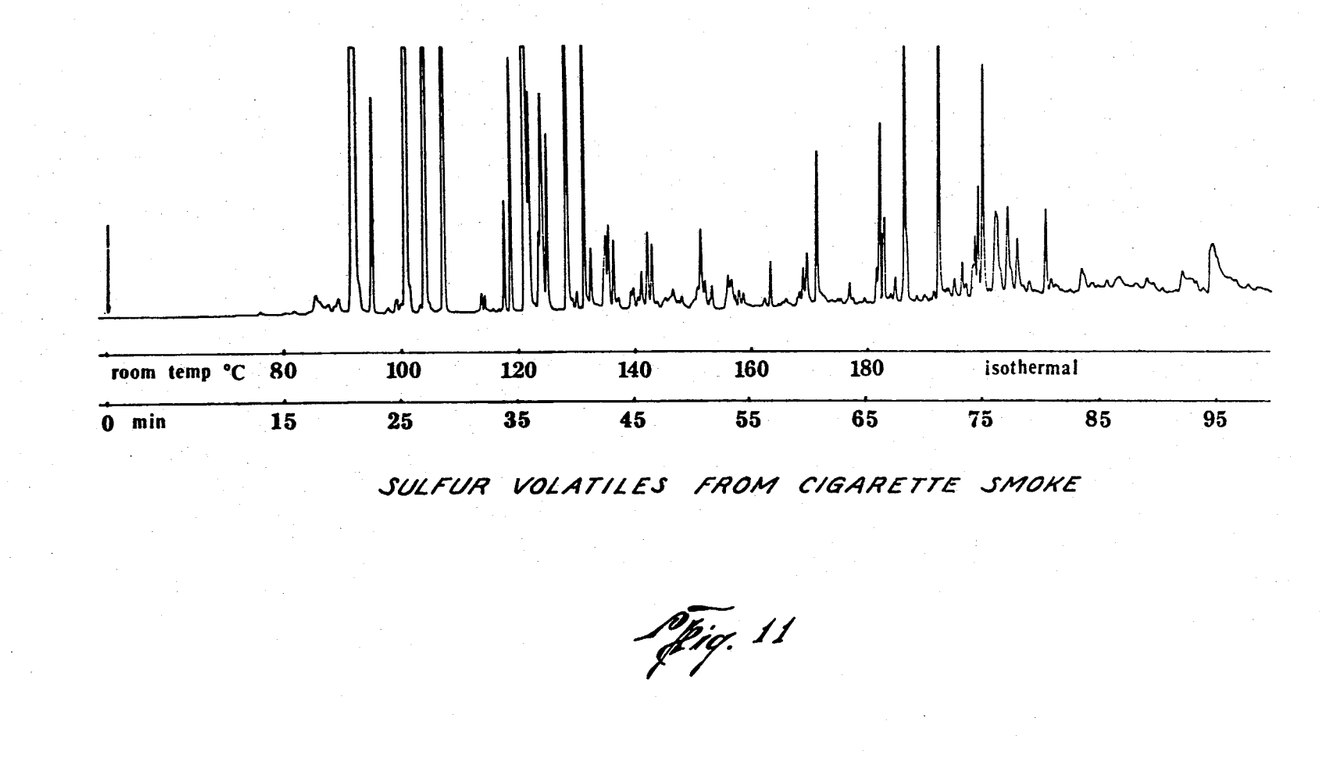
FIG. 11 is a profile of volatiles in cigarette smoke.

In this example samples of cigarette smoke and perfume are sampled, transferred and analyzed as described in Examples 5 and 6. Profiles were obtained and are compared or matched up with chromatographic profiles of samples from standards of cigarette smoke and the perfume, the standard profile being used as a basis of comparison for quality control so that suitable processing adjustments can be made for purposes of quality control. The sulfur profiles are particularly revealing for cigarette smoke comparisons, and such a profile is illustrated in FIG. 11.

In all of the foregoing examples, the flow rates for and temperatures of desorption may vary as desired. For urine samples, however, desorbing between temperatures of 230°-300° C. is preferred. For determination of $H_2S$ and $SO_2$ desorbing at ambient temperatures is satisfactory. At temperatures of the order of 400° C., various steroids and polynuclear aromatics (hydrocarbons) can be analyzed and determined, care being taken as pyrolysis may occur if a temperature of 400° C. is maintained for a long period of time.

EXAMPLE 12

During the recent Skylab mission traps containing poly 2,6-diphenyl-p-phenylene oxide were used to trap samples of the air in the Orbital Workshop at various times during the mission. This was accomplished by exposing the trap insert to the vacuum of space thereby drawing a sample of the air in the Orbital Workshop past the trap due to the differential in pressure between the Workshop and space. It was found from post-flight analyses of the samples that volatile organic compounds were present in the air and differences in volatiles present in the air were determined in samples collected at different times.

The above specific examples of applications and uses of the method and apparatus fully illustrate the invention, but are not exhaustive. In detecting disease and monitoring its treatment profiles of volatiles from blood, cerrebral spinal fluids and tissue culture may be made and compared to standard or reference profiles.

In using blood as the sample, it has been found that the profiles of plasma and serum are the same. Advantageously, by using headspace gas adsorption according to this invention, very small samples of blood can be used as contrasted to use of relatively large samples, a pint of blood, in other methods. Reproducibility is excellent and blood is not subject to external conditions to the same extent as urine. Samples of blood may be used for detectng metabolic disorders, such as diabetes, lukemia, cirrhosis of the liver, schizophrenia, etc.

Similarly, other body fluids, such as saliva and cerrebral spinal fluid, and tissue culture may be used as the sample. Forensic applications are also possible. For example, compounds can be added to products and profiles made, thus making a "fingerprint" of the product which cannot be erased and would establish its identity. Identification of products for scientific and criminal detection purposes is possible by making a profile of an object and comparing it to a reference. In addition, analyses of closed environments, such as in spacecraft, aircraft, submarines and other enclosures can be made by trapping samples and sending them to a laboratory, as well as analyses for other purposes.

From the foregoing, it is seen that the ability of the present invention to identify and determine the quantity of specific organic volatiles which may be in trace amounts, for example, a few parts in a billion, makes it an excellent research and analytical tool for not only the fields mentioned above, but for many other fields of use.

Accordingly, while presently-preferred embodiments and a number of examples and applications of the present invention have been given for the purposes of disclosure, changes, and additional applications and uses may be made.

Accordingly, the present invention is well suited and adapted to attain the objects and ends and has the advantages and features mentioned as well as others inherent therein.

What is claimed is:

1. In a method of analysis in a gas chromatographic system for volatile organic compounds in a sample, the step of remotely and independently of the gas chromatographic system trapping the volatile organic compounds in the sample by adsorbing them on a porous polymer consisting essentially of 2,6-diphenylp-phenylene oxide, said polymer having properties of high affinity for organic volatiles being hydrophobic, having temperature stability up to about 400° C., having good desorptivity, and being relatively inert to the sample, whereby such trapped volatile organic compounds are retained, for later chromatographic analysis.

2. The method of claim 1 where, the sample is selected from the group consisting of body fluids and tissue culture.

3. The method of claim 1 where, the sample is air.

4. The method of claim 1 where, the sample is water.

5. The method of claim 1 where, the sample is selected from the group consisting of food and drink.

6. The method of claim 1 where, the sample is smoke.

7. The method of claim 1 further comprising the steps of:
subsequent desorbing, without artifacts, the adsorbed volatile organic compounds from the porous polymer at temperatures from ambient up to about 400° c.,
collecting the desorbed volatile organic compounds, and,
chromatographic analyzing of the volatile organic compounds.

8. The method of claim 7 where, the analyzing is by obtaining a profile of the desorbed volatile organic compounds and comparing the profile of the desorbed volatile organic compounds with a profile of volatile organic compounds from a reference.

9. The method of claim 8 where, the sample is selected from the group consisting of body fluids and tissue culture.

10. The method of claim 8 where, the sample is air.

11. The method of claim 8 where, the sample is water.

12. The method of claim 8 where, the sample is smoke.

13. The method of claim 8 where, the sample is selected from the group consisting of food and drink.

14. The method of claim 8 where, the sample and the reference are selected from the group consisting of body fluids and tissue culture.

15. The method of claim 8 where, the sample and the reference are smoke.

16. The method of claim 8 where, the sample and the reference are air.

17. The method of claim 8 where, the sample and the reference are water.

18. The method of claim 8 where, the sample and the reference are selected from the group consisting of food and drink.

19. The method of claim 14 where the desorbing is at temperatures from about 230° C. up to about 400° C., a profile of the desorbed volatile organic compounds is obtained, and
the profile is compared with a profile of volatile organic compounds from a reference sample.

20. The method of claim 19 where, the desorbing is at temperatures from about 230° C. to about 300° C.

21. The method of claim 20 where, the sample and the reference sample are selected from the group consisting of blood plasma and blood serum.

22. The method of claim 20 where, the sample and the reference sample are urine.

23. The method of claim 8 where the volatile organic compounds are from the headspace between a sample of a processed product and the adsorbent.

24. The method of claim 8 where the volatile organic compounds are from the headspace between a sample selected from the group consisting of body fluids and tissue culture and the adsorbent.

25. The method of claim 1 where, the adsorbing of the volatile organic compounds on the polymer is at temperatures from ambient room temperature and below.

26. The method of claim 1, wherein the polymer is encased in a supportive tube like body.

27. The method of claim 26 wherein the tube like body after adsorption of the volatile organic compounds is enclosed is a sealable container for transportation or storage.

28. A method of analyzing volatile organic compounds in a sample comprising,
trapping the volatile organic compounds by adsorbing them on a porous polymer consisting essentially of 2,6-diphenyl-p-phenylene oxide in a trap,
connecting the trap to a cryogenically cooled precolumn of a gas chromatograph thermally desorbing without artifacts the adsorbed volatile organic compounds from the polymer in the trap, and transferring them to the precolumn and,
transferring the volatile organic compounds from the precolumn to a separating column of the gas chromatograph for analysis.

29. The method of claim 28 where, the separating column is a thin-walled capillary tube formed of nickel etched with a solution of concentrated nitric and acetic acids.

30. The method of claim 28 where, the desorbing of the volatile organic compounds to the precolumn is by heating the porous polymer to temperatures up to about 400° C.

31. The method of claim 30 where, the sample is selected from the group consisting of body fluids and tissue culture.

32. The method of claim 30 where, the sample is air.

33. The method of claim 30 where, the sample is water.

34. The method of claim 30 where, the sample is selected from the group consisting of food and drink.

35. The method of claim 30 where, the sample is smoke.

36. The method of claim 28 where, the desorbing of the volatile organic compounds is by heating the porous polymer to temperatures up to about 400° C.

* * * * *